(12) United States Patent
Moss et al.

(10) Patent No.: US 10,607,590 B2
(45) Date of Patent: Mar. 31, 2020

(54) MASKING NOISES FROM MEDICAL DEVICES, INCLUDING DIALYSIS MACHINES

(71) Applicant: Fresenius Medical Care Holdings, Inc., Waltham, MA (US)

(72) Inventors: Jon F. Moss, Antioch, CA (US); Bert D. Egley, Walnut Creek, CA (US); Daniel H. Schmidt, Petaluma, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 435 days.

(21) Appl. No.: 15/695,247

(22) Filed: Sep. 5, 2017

(65) Prior Publication Data

US 2019/0073990 A1    Mar. 7, 2019

(51) Int. Cl.
| | | |
|---|---|---|
| *H04R 3/00* | (2006.01) | |
| *H04R 1/08* | (2006.01) | |
| *G10K 11/175* | (2006.01) | |
| *A61B 5/00* | (2006.01) | |
| *A61M 21/02* | (2006.01) | |

(Continued)

(52) U.S. Cl.
CPC .......... *G10K 11/175* (2013.01); *A61B 5/4812* (2013.01); *A61M 1/14* (2013.01); *A61M 21/02* (2013.01); *A61M 2021/0027* (2013.01); *A61M 2205/3561* (2013.01); *A61M 2205/3584* (2013.01); *A61M 2205/42* (2013.01); *A61M 2205/505* (2013.01); *A61M 2205/52* (2013.01); *A61M 2230/06* (2013.01); *A61M 2230/42* (2013.01); *G10K 2210/116* (2013.01); *G10K 2210/3056* (2013.01); *G10K 2210/30351* (2013.01); *G10K 2210/3222* (2013.01)

(58) Field of Classification Search
CPC .......... G10K 11/175; G10K 11/17827; G10K 2210/116; G10K 2210/1161; G10K 2210/30351; G10K 2210/3056; G10K 2210/3222; A61B 5/4812; A61B 5/4815; A61B 5/4818; A61M 1/14; A61M 21/02; A61M 2021/0027; A61M 2205/3561; A61M 2205/3584; A61M 2205/42; A61M 2205/505; A61M 2205/52; A61M 2230/06; A61M 2230/42
USPC .......... 381/73.1, 94.1–94.8, 71.1–71.14, 72
See application file for complete search history.

(56) References Cited

U.S. PATENT DOCUMENTS

| | | |
|---|---|---|
| 3,879,578 A | 4/1975 | Wildi |
| 5,313,945 A | 5/1994 | Friedlander |
| 5,427,102 A | 6/1995 | Shimode et al. |

(Continued)

OTHER PUBLICATIONS

International Search Report and Written Opinion for application No. PCT/US2018/049352, dated Dec. 5, 2018, 17 pages.

*Primary Examiner* — Xu Mei (57) ABSTRACT

A method and device for masking noise from a dialysis machine, as an example of a medical device, includes tubing or a fluid container, or both, being connectable to a patient for flowing fluid to or from the patient, and one or more sensors configured to detect one or more patient parameters. The dialysis machine further includes a controller configured to determine a sleep state of the patient based on the one or more patient parameters detected by the plurality of sensors, and adjust a masking sound in response to the sleep state of the patient. The masking sound is activatable in response to noise generated during operation of the dialysis machine.

30 Claims, 4 Drawing Sheets

(51) Int. Cl.
*A61M 1/14* (2006.01)
*A61M 21/00* (2006.01)

(56) References Cited

U.S. PATENT DOCUMENTS

| | | | | |
|---|---|---|---|---|
| 5,444,786 | A * | 8/1995 | Raviv | A61F 5/56 381/71.14 |
| 6,188,771 | B1 | 2/2001 | Horrall | |
| 6,897,781 | B2 | 5/2005 | Cooper et al. | |
| 6,954,666 | B2 * | 10/2005 | Bechtold | A61B 5/055 600/410 |
| 7,804,964 | B2 * | 9/2010 | Schreiber | G10K 11/175 381/72 |
| 8,069,852 | B2 | 12/2011 | Burton et al. | |
| 8,798,284 | B2 | 8/2014 | Cartwright et al. | |
| 2002/0169384 | A1 * | 11/2002 | Kowallik | A61M 16/026 600/529 |
| 2008/0110459 | A1 | 5/2008 | Farbarik | |
| 2008/0243211 | A1 | 10/2008 | Cartwright et al. | |
| 2011/0180480 | A1 | 7/2011 | Kloeffel et al. | |
| 2012/0157870 | A1 * | 6/2012 | Derkx | A61B 7/003 600/529 |
| 2015/0179161 | A1 * | 6/2015 | Fujiwara | G10K 15/04 381/98 |
| 2015/0258301 | A1 * | 9/2015 | Trivedi | G06F 16/636 600/28 |
| 2015/0313535 | A1 * | 11/2015 | Alshaer | A61B 5/4812 600/529 |
| 2016/0055842 | A1 | 2/2016 | DeFranks et al. | |
| 2016/0066716 | A1 | 3/2016 | Rao | |
| 2017/0367646 | A1 * | 12/2017 | Schmidt | A61B 5/746 |
| 2018/0078732 | A1 * | 3/2018 | Keshavan | A61M 21/02 |

* cited by examiner

MASKING NOISES FROM MEDICAL DEVICES, INCLUDING DIALYSIS MACHINES

FIELD OF THE DISCLOSURE

The disclosure generally relates to medical devices, including dialysis machines, and more particularly to methods and devices for masking noises from medical devices, including dialysis machines.

BACKGROUND OF THE INVENTION

It is known to mask a machine sound by using the original sound itself, or by separately generating cancelling noise signals to cancel undesirable sounds. Some medical machines may generate loud noises during a medical procedure which may increase a patient's discomfort, especially when the medical procedure is prolonged. Noise cancellation during the medical procedure may improve a patient's experience. However, it may be disadvantageous if the noise cancellation is only related to the operation of the medical machine with no reliance on any patient parameters, if the masking may be needed only for part of the operation, or if the noise levels shift during the medical procedure. It is not desirable to generate a constant noise cancelling frequency when the procedure is several hours long and may occur when a patient is attempting to sleep.

Noise cancellation may also be utilized to reduce ambient sounds in a medical environment (e.g., a hospital, nursing home, or care center), but may be disadvantageous in that it is not related to operation of a medical machine. Based on a patient's physical movements in a bed, for example, noise cancellation may be decreased to encourage regular patient movement during a sleep cycle to reduce the likelihood of bed sores. However, it may be disadvantageous when noise cancellation is not associated with a medical machine because noise generated by the medical machine is typically positioned nearer the patient and may be at a more noticeable volume than other sounds associated in a medical facility.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an embodiment of the present disclosure, a dialysis machine may include a tubing or a fluid container, or both, being connectable to a patient for flowing fluid to or from the patient, one or more sensors configured to detect one or more patient parameters, and a controller. The controller may be configured to determine a sleep state of the patient based on the one or more patient parameters detected by the one or more sensors, and adjust a masking sound in response to the sleep state of the patient. The masking sound may be activatable in response to noise generated during operation of the dialysis machine.

According to an embodiment of the present disclosure, a method for operating a dialysis machine for a patient being connected to tubing or a fluid container, or both, for flowing fluid to or from the patient may include monitoring one or more patient parameters by one or more sensors and initiating a masking sound in response to noise generated during operation of the dialysis machine. The method may further include determining a sleep state of the patient by a controller, based on the one or more patient parameters detected by the one or more sensors and adjusting the masking sound by the controller in response to the sleep state of the patient.

BRIEF DESCRIPTION OF THE DRAWINGS

By way of example, specific embodiments of the disclosed methods and devices will now be described, with reference to the accompanying drawings, in which.

DETAILED DESCRIPTION

The present embodiments will now be described more fully hereinafter with reference to the accompanying drawings, in which several exemplary embodiments of dialysis machines, systems, and methods, are shown. The subject matter of the present disclosure, however, may be embodied in many different forms and types of methods and devices for dialysis machines and other potential medical devices and treatments, and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Exemplary embodiments of a dialysis machine in accordance with the present disclosure may include components, systems, and processes for masking noise during operation. For example, a home dialysis machine such as a peritoneal dialysis machine or a hemodialysis machine may be set up by a user to operate overnight, while a patient is sleeping. Masking noises associated with operation of the dialysis machine may improve a patient's sleep cycle, and may be tailored based on feedback of one or more patient parameters that are monitored during the dialysis operation. This is an improvement over known noise cancellation devices described above in that masking may be adjusted based on the patient's sleep status. For example, masking may be increased when a monitored parameter indicates a patient is waking up, and decreased or turned off when the monitored parameter indicates a patient has entered a deep sleep state. Since masking sounds may disturb the sleep of other persons in a room, e.g., a co-sleeper, it may be advantageous for a machine to decrease and/or turn off the masking altogether so long as the patient parameters indicate a patient is in a deep sleep state.

An exemplary embodiment may capture and analyze information from sensors in communication with the treatment system and/or a treatment controller. An example treatment system may include embedded pressure sensors that monitor pressure at a cassette pump associated with a peritoneal dialysis system (e.g., the Liberty® Cycler produced by Fresenius Medical Care may include a pressure sensor located on the cassette pump plate inside a machine door—described in greater detail with reference to FIG. 2 below). According to one embodiment, the patient pressure sensor senses pressure inside the patient's peritoneum and may be used to detect patient biological parameters corresponding to sleep (e.g., lowered heart rate, or lowered respiration rate). In one example, the pressure sensor is used to detect pressure fluctuations triggered by the patient's heart beat or breathing. Likewise, the pressure sensor may detect patient parameters associated with any changes in sleep state, including awakening states (e.g., the pressure sensor may detect increased heart rate, increased respiration, and movement during sleep). Various embodiments may incorporate information from multiple sensors to establish reliable information on the patient's sleep state. For example, patients may be provided with heart rate and/or respirations sensors to connect to the treatment system.

In another embodiment, the treatment system may connect to a mobile device (e.g., a smart phone, a wearable device, an activity tracking device, a sleep manager, etc.) or other fitness devices or the like and receive sensor data regarding the patient. The sensors from such devices may also provide information on the noise produced by the treatment system. The dialysis machine may therefore adjust masking based on these monitored patient parameters. For example, in response to a heart rate increasing, indicating a patient may be awakened or awakening from a sleeping state, such as a deep sleep state, a masking sound may increase, thereby detracting noise generated by the dialysis machine. Similarly, in response to a slower respiration rate indicating the patient is entering a deep sleep state, the masking may decrease or turn off.

Figure 1:
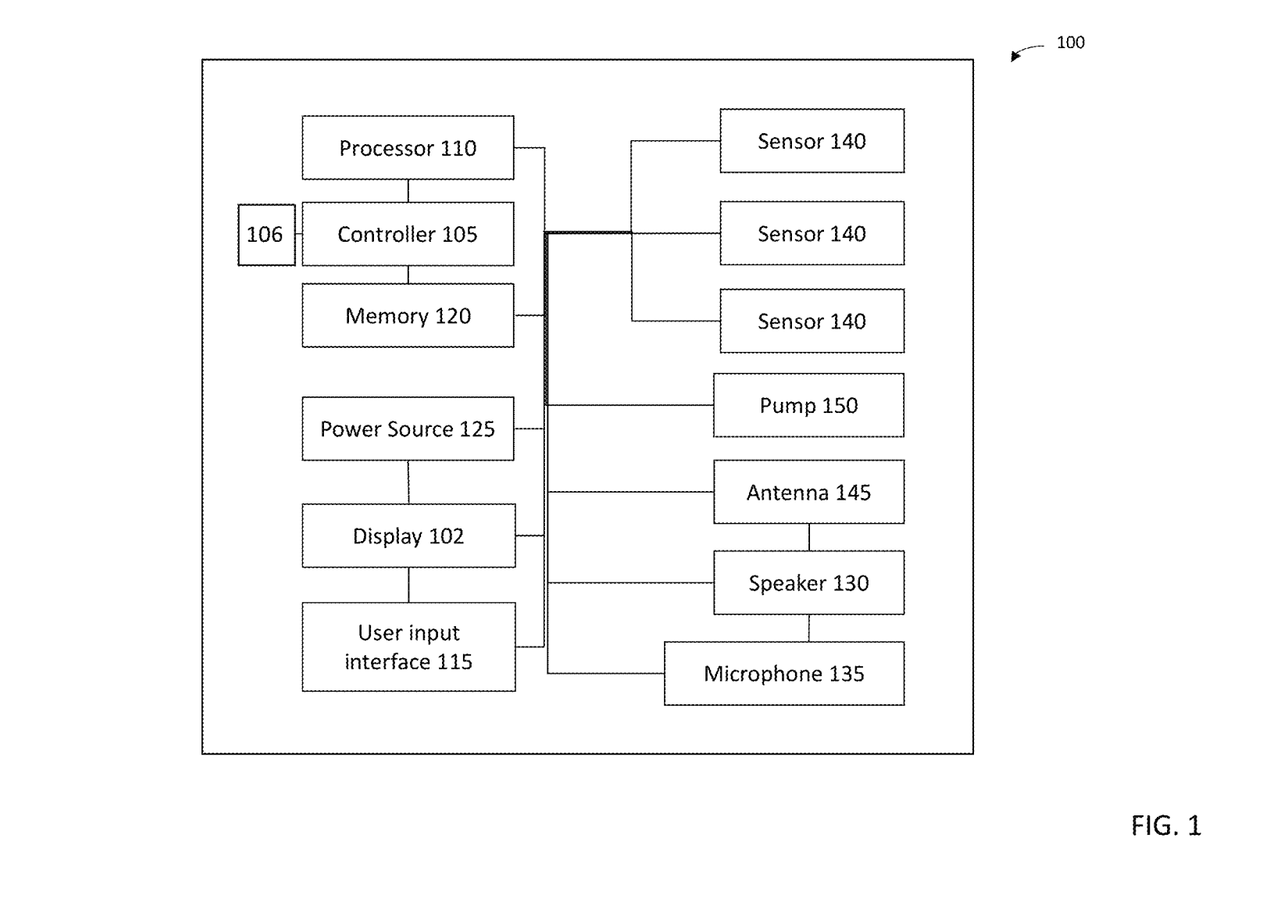
FIG. 1 is a block diagram illustrating an exemplary embodiment of a machine controller in accordance with the present disclosure.

Referring to FIG. 1, a schematic of an exemplary embodiment of a dialysis machine 100 and a controller 105 in accordance with the present disclosure are shown. The machine 100 may be a home dialysis machine, e.g., a peritoneal dialysis machine, or a home hemodialysis machine, although it is understood that the machine may be any type of medical device that generates a noise during operation. The controller 105 may automatically control execution of a treatment function during a course of dialysis treatment. The controller 105 may be operatively connected to sensors 140 and deliver one or more signals to execute one or more treatment functions or a course of treatment associated with various treatment systems. In some embodiments a treatment system may be a dialysis machine, including but not limited to a peritoneal dialysis machine and a home hemodialysis machine, used for performing a dialysis treatment on a patient. Communication between the controller 105 and the treatment system may be bi-directional, whereby the treatment system acknowledges control signals, and/or may provide state information associated with the treatment system and/or requested operations. For example, system state information may include a state associated with specific operations to be executed by the treatment system (e.g., trigger pump to deliver dialysate, trigger pumps and/or compressors to deliver filtered blood, and the like) and a status associated with specific operations (e.g., ready to execute, executing, completed, successfully completed, queued for execution, waiting for control signal, and the like).

The controller 105 may manage treatment execution such that the noise levels generated during treatment may be masked by masking sounds. For example, the dialysis machine 100 may include a pump 150 operatively connected to the controller 105. During a treatment operation, the controller 105 may control the pump 150 for pumping fluid, e.g., fresh and spent dialysate, to and from a patient. The controller 105 may also be operatively connected to one or more speakers 130 and one or more microphones 135 disposed in the machine 100. The microphone 135 may be arranged to detect a sound level, or frequency, generated by the machine 100. The controller 105 may determine a canceling sound based on a calculated frequency level and/or user-based selections, so that the sound level generated by the machine 100 is reduced or canceled. In some embodiments, the machine 100 may be configured to play music or other sounds selected by a user through a user input interface 115 stored in a memory 120 of the machine 100 and played via the speaker 130, including but not limited to music and pre-recorded sounds such as nature sounds, animal sounds, and white noise. The user input interface 115 may include a combination of hardware and software components that allow the controller 105 to communicate with an external entity, such as a patient or other user. These components may be configured to receive information from actions such as physical movement or gestures and verbal intonation. In addition, the components of the user input interface 115 may provide information to external entities. Examples of the components that may be employed within the user input interface 115 include keypads, buttons, microphones, touch screens, gesture recognition devices, display screens, and speakers.

The machine 100 may also be wirelessly connectable via the antenna 145 for remote communication, so that a user may be able to customize to their own sleeping preferences from a remote device. For example, a user may desire to mask noise generated by the machine 100 and fall asleep listening to music, a podcast, an audio book, white noise, pre-recorded sounds, noise cancelling frequency, and/or other soothing sounds, or combinations thereof. This may be advantageous for relaxing a patient during a treatment operation. The sound selection may be displayed on the display 102 for user selection and/or confirmation. The user may desire to listen to music until they have fallen asleep, and then desire to have white noise or other soothing sounds play for the duration of the treatment. Additionally, combinations of the same sound selection may be available to a user, e.g., a user may desire a particular type of music initially, and then transition to another type of music during dialysis treatment. According to embodiments of the present disclosure, a masking sound, combinations of masking sounds, or a series of different masking sounds, may be delivered at various stages of the dialysis operation. As such, combinations of music, a podcast, an audio book, white noise, pre-recorded sounds, noise cancelling frequency, and/or other soothing sounds may be selectable and adjustable during the dialysis operation.

In some embodiments, masking sounds may be generated by components of the machine 100. For example, one or more fans (not shown) may be disposed in or on the machine 100, associated with the power source 125 and/or a processor 110. Additionally, an air compressor (not shown) may be included that is associated with the pump 150. The controller 105 may operate the pumps, the fans, and/or the air compressor, or combinations thereof, at a frequency level so as to generate a noise cancelling masking sound without additional sounds emanating from the speaker 130. For example, the controller 105 may operator the components (e.g., pumps, fans, air compressors) individually, together, and/or intermittently with each other to generate a noise cancelling masking sound. This may be advantageous as a cost-savings, to reduce the number and complexity of components included in the machine 100.

As shown in FIG. 1, sensors 140 may be included for monitoring one or more patient parameters and be operatively connected to the controller 105, processor 110, and memory 120. The processor 110 may be configured to execute an operating system, which may provide platform services to application software, e.g., for operating the dialysis machine 100 and monitoring noise levels. These platform services may include inter-process and network communication, file system management and standard database manipulation. One or more of many operating systems may be used, and examples are not limited to any particular operating system or operating system characteristic. In some examples, the processor 110 may be configured to execute a real-time operating system (RTOS), such as RTLinux, or a non-real time operating system, such as BSD or GNU/Linux. According to a variety of examples, the processor 110 may be a commercially available processor such as a processor manufactured by INTEL, AMD, MOTOROLA, or FREESCALE, or combinations thereof. However, the processor 110 may be any type of processor, multiprocessor or controller, whether commercially available or specially manufactured. For instance, according to one example, the processor 110 may include an MPC823 microprocessor manufactured by MOTOROLA.

The memory 120 may include a computer readable and writeable nonvolatile data storage medium configured to store non-transitory instructions and data. In addition, the memory 120 may include a processor memory that stores data during operation of the processor 110. In some examples, the processor memory includes a relatively high performance, volatile, random access memory such as dynamic random access memory (DRAM), static memory (SRAM), or synchronous DRAM. However, the processor memory may include any device for storing data, such as a non-volatile memory, with sufficient throughput and storage capacity to support the functions described herein. Further, examples are not limited to a particular memory, memory system, or data storage system.

The instructions stored on the memory 120 may include executable programs or other code that may be executed by the processor 110. The instructions may be persistently stored as encoded signals, and the instructions may cause the processor 110 to perform the functions described herein. The memory 120 may include information that is recorded, on or in, the medium, and this information may be processed by the processor 110 during execution of instructions. The memory 120 may also include, for example, specification of data records for user timing requirements, noise levels produced during treatment, noise levels produced during respective treatment operation(s), timing for treatment and/or operations, historic sleep state information, historic sensor information, patient sleep state models. The medium may, for example, be optical disk, magnetic disk or flash memory, among others, and may be permanently affixed to, or removable from, the controller 105.

A pressure sensor may be included for monitoring fluid pressure of the machine 100, although the sensors 140 may also include any of a heart rate sensor, a respiration sensor, a temperature sensor, a video sensor, a thermal imaging sensor, an electroencephalogram sensor, a motion sensor, audio sensor, an accelerometer, or capacitance sensor. It is appreciated that the sensors 140 may include sensors with varying sampling rates, including wireless sensors. Based on data monitored by the sensors 140, patient parameters such as a heart rate and a respiration rate may be determined by the controller 105. A patient's heart rate and/or respiration rate may be continually monitored by the sensors 140 to determine when a patient has fallen asleep and/or entered a deep sleep state. The sensors 140 may periodically monitor patient parameters, may continuously monitor patient parameters, and/or may change from continuous to periodic monitoring, or vice versa, throughout a dialysis operation. In some embodiments, the machine 100 may have pre-determined limits of any of a fluid pressure, a heart rate, and/or a respiration rate, or combinations thereof, for determining when a masking sound may be decreased or stopped. In other embodiments, the machine 100 may have individual patient data from previous cycles, so that the machine 100 is customizable based on an individual patient's sleep pattern. In some embodiments, the controller 105, processor 110, and memory 120 may be configured to model a patient sleep cycle (e.g., progression through sleep states), and use the model to extrapolate an expected sleep state and time for that sleep state. For example, sensors 140 may detect readings and timings associated with determined sleep states to build the sleep model.

In some embodiments, the processor 110 may be configured to compare sensor readings to stored data which may include threshold values or ranges of values for determining stages, or states, of sleep. Stages of sleep are defined to include multiple stages (e.g., stage 1—light sleep, stage 2—eye movement stops, stage 3 and/or stage 4 (stage 3 and 4 have been combined in some research)—deep sleep, and rapid eye movement ("REM") sleep, respectively). In some examples, the controller 105 may determine a stage of sleep, including determining that the patient is in a deep sleep state (e.g., stages 3, 4, or REM sleep). The determination of sleep state may be used by the controller to initiate treatment (e.g., start dialysis treatment at deep sleep state) and/or adjust masking.

For example, the processor 110 may calculate a decrease in a patient's respiration rate of 10%, 15%, 20% or more to identify entry into a deep sleep state. The processor 110 may also calculate a decrease in respiration based on monitoring the sensors 140, and a respiration rate may become regular in frequency as sleep progresses until reaching REM sleep. The processor 110 may be configured to identify the changes in respiration frequency.

In some embodiments, a decrease in heart rate may be used to determine a sleep state of a patient, for example, 5%, 10% or more may indicate a deep sleep state. As described above, a pressure sensor 140 may monitor a fluid pressure of the machine 100, for example, a fluid pressure of a patient's peritoneal cavity, and correlate fluctuations in the fluid pressure with a determined heart rate and/or respiration rate to yield a patient sleep state. In other embodiments, the sensors 140 may monitor any of temperature readings, changes in degree in movement in bed, and the like, and may be used to identify when a patient has achieved a deep sleep (alone or in combination). It is understood that the machine 100 may determine a patient's sleep state using any known technique.

The controller 105 may also coordinate analysis of patient sleep state with external systems via the antenna 145. For example, the controller 105 may coordinate with other sensor systems, sleep management system, activity monitoring devices, fitness sensors, and the like. Example of sleep trackers include products produced by FITBIT, JAWBONE, SLEEPTRACKER, LARK, MELLON, ZEO, SLEEP CYCLE, SLEEP BOT, and SLEEP AS ANDROID, among other options. In some examples, the controller 105 may evaluate the assessment of deep sleep versus light sleep and incorporate such assessments into a determination of the patient's sleep state. In some embodiments, the controller 105 may be configured to identify light versus deep sleep and manage treatment and/or masking using a two state model, as well as models with more sleep states.

The controller 105 may be configured to initiate a dialysis operation of the dialysis machine 100, and may substantially simultaneously initiate a masking sound from the machine 100 as noise is generated as the machine begins operating. As described, a user may operate a home dialysis machine overnight. Masking may therefore be necessary for the dialysis operation at the beginning of the cycle before a patient has fallen asleep, and throughout an early sleep state to prevent a patient from waking up. As the patient enters a deep sleep state, the masking sounds may be decreased or turned off altogether. In some embodiments, when the dialysis operation generates a noise above a threshold noise level (e.g., 30 decibels (dB), 35 dB, 40 dB, etc.), e.g., at a certain point in the dialysis operation, the machine 100 may be configured to initiate or increase a masking sound so that the patient's sleep cycle is undisturbed. In some embodiments, the controller 105 and/or processor 110 may generate or access an expected course of treatment timeline that establishes sound levels produced at given times, time periods, and/or for specific operations during a course of treatment. The controller 105 may manage treatment execution, so that masking is applied at appropriate points during the dialysis operation. The controller 105 and/or the machine 100 may also be configured to learn from prior execution data to identify times when masking is most desirable to ensure sleep is uninterrupted and/or to improve a patient sleep model.

In some embodiments, the controller 105, processor 110 and/or memory 120 may utilize predefined noise levels stored in the memory 120 associated with the controller 105. For example, a database may maintain predefined noise levels, and associated masking response levels needed to ensure the patient sleep cycle remains undisturbed. The controller 105 and the processor 110 may also use real time sound readings captured by microphones 135 or other audio sensors. In other embodiments, treatment timelines or noise levels associated with specific operations may be updated based on readings from the microphones 135 and/or audio sensors, and updated volumes may be used for determining the appropriate masking sound levels.

User specified parameters may be input directly in the machine 100 by the user input interface 115, which may be a graphical user interface (GUI) or touch button interfaces for selecting operation parameters, including a masking sound selection as described above. In some embodiments, the user input interface 115 may be connectable with a remote device for receiving a user selection. For example, a mobile phone, tablet, laptop, and computer may be connectable to the machine 100 so a desired masking sound may be selected for use during the dialysis operation. The selection may be viewable on the user input interface 115 for confirmation, and the desired masking sound may be streamed from the remote device, or uploaded to the memory 120.

The controller 105 may also be configured to decrease or altogether stop a masking sound in the event of an unsafe condition so that a patient may be encouraged to awaken. For example, the sensors 140 may detect an unsafe condition, including but not limited to a low heart rate, a low respiration rate, a high heart rate, a high respiration rate, low/high temperature, such that the monitored patient parameters are outside of acceptable conditions for a safe dialysis treatment operation. Additionally, the machine 100 may detect a malfunction, including but not limited to a leak, a pumping failure, and an improper connection, which may necessitate a shutdown of operation. In the event an unsafe condition is detected, the controller 105 may initiate or suspend any treatment, stopping or decreasing masking sounds, and generate audio and/or visual alarms.

Figure 2:
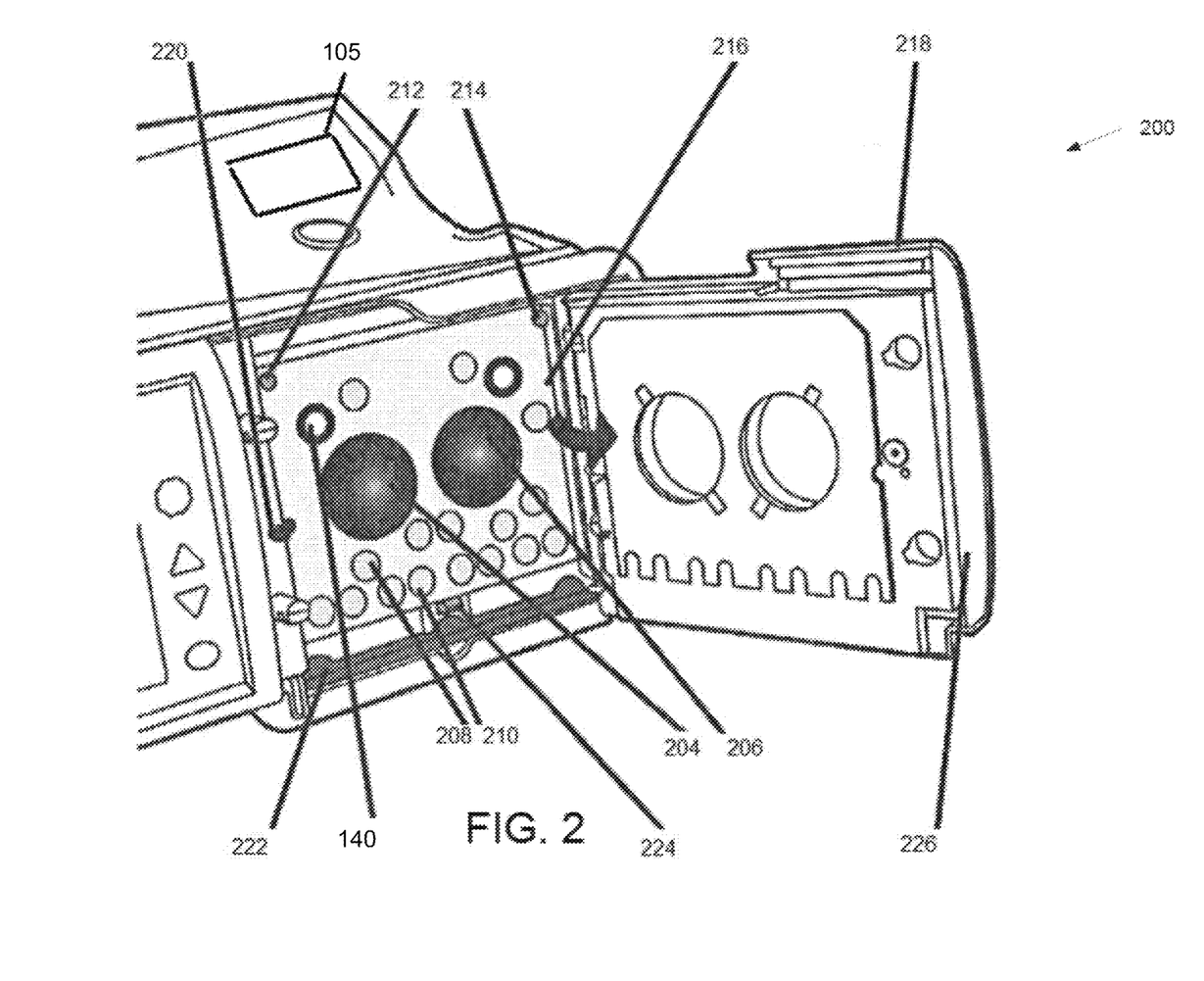
FIG. 2 illustrates an exemplary embodiment of a portion of a dialysis machine in accordance with the present disclosure.

Referring now to FIG. 2, an exemplary embodiment of a portion of a dialysis machine 200 in accordance with the present disclosure is shown. The machine 200 may include the components described above with respect to the schematic of the machine 100 illustrated in FIG. 1. The machine 200 may be configured to provide home dialysis treatment, for example, peritoneal dialysis. The machine 200 may manage flowing dialysate into a patient's abdomen, and removal of the used dialysate and waste after a predetermined amount of time. While the dialysate is present in a peritoneal cavity of the patient, the dialysate may absorb contaminants and/or particulates from the patient's blood. Peritoneal dialysis uses the patient's peritoneum in the abdomen as a membrane across which fluids and dissolved substances (e.g., electrolytes, urea, glucose, albumin, osmotically active particles, and other small molecules) are exchanged from the blood.

The machine 200 may include a pressure sensor 140 for providing readings on the fluid (e.g., dialysate). As discussed above, pressure readings may be taken at various intervals during a dialysis operation to provide fluctuation data from which to extrapolate, for example, a patient heart rate and/or a patient respiration rate. In some embodiments, additional instruments or sensors may be employed to provide direct measurement of heart rate, respiration rate, and/or other biological characteristics pertinent to determining a sleep state.

The machine 200 may operate pump heads 204 and 206 to move the fluid. The pump heads apply force to a cassette (not shown) that connect a fluid reservoir to a catheter at the patient's peritoneum. By operation of the pump heads 204 and 206, fresh dialysate may be drawn from a fluid reservoir and introduced into the patient's peritoneum. Likewise, pump heads 204 and 206 may draw fluid from the patient's peritoneum into a fluid reservoir. Multiple reservoirs may be used including a clean fluid reservoir and a waste fluid reservoir. Operation of the pump heads in conjunction with valves (e.g., valves 208 and 210) controls delivery or retrieval of fluid.

In some embodiments, cassette guide pins 212 and 214 are present to ensure proper alignment of a cassette when inserted into the machine 200. A cassette pump plate 216 contains the pump mechanism and provides openings for the pump heads to operate on an inserted cassette. The door latch 218, door sensor 220, safety clamp 222, and cassette catch 224 are configured to ensure proper alignment and engagement with a cassette once inserted and once the cassette door 226 is closed.

The controller 105 may be disposed in the machine 100, 200 or may be coupled to the machine 100, 200, or other external systems, via a communication port or wireless communication links, shown schematically as communication element 106 (see FIG. 1). According to various examples, the communication element 106 may support a variety of one or more standards and protocols, examples of which include USB, WiFi, TCP/IP, Ethernet, Bluetooth, Zigbee, CAN-bus, IP, IPV6, UDP, UTN, HTTP, HTTPS, FTP, SNMP, CDMA, NMEA and/or GSM. As a component disposed within the machine 200, the controller 105 may be operatively connected to any one or more of the sensors 140, pump 150, pump heads 204, 206, and the like. The controller 105 may communicate control signals or triggering voltages to the components of the machine 200. As discussed, exemplary embodiments of the controller 105 may include wireless communication interfaces. The controller 105 may detect remote devices to determine if any remote sensors are available to augment any sensor data being used to evaluate the patient. In some embodiments, the controller 105 may detect and communicate with one or more remote devices to communicate with available sensors 140 that may individually or collectively sense patient parameters pertinent to determining a sleep state in the patient. For example, remote devices may include smart phone microphones, video cameras, cameras, thermal imaging cameras, in bed sensors, sleep manager applications and sensors, web cameras, fitness sensors, stand-alone sensors, and the like.

In some examples, the controller 105 may also manage the dialysis operation on the basis of a co-sleeper sleep state. As described above, the noise generated by the machine 100, 200 may affect persons in the vicinity of the machine as well as the patient. "Vicinity" is understood to be in the same room and/or in the same bed with the patient. Each of the functions and sleep state analysis operations described above may be used to determine a sleep state for one or more co-sleepers, which may be used to alter operations and/or adjust masking sounds of the treatment system based on sleep states of both the patient and the additional sleeper even though they may be unconnected to tubing and/or a fluid bag or other fluid container. In an embodiment, a fluid container may include a container in which dry concentrates are mixed with water to generate dialysate suitable for a dialysis treatment. Although a co-sleeper need not be receiving dialysis treatment, and therefore may not have certain data available (e.g., peritoneal pressure readings from the pressure sensor 140), physiological data with respect to the co-sleeper may be available from external sensors described above. The machine 100, 200 may then be able to monitor and adjust the masking sound in accordance with both the patient and a co-sleeper throughout the dialysis operation.

Figure 3:
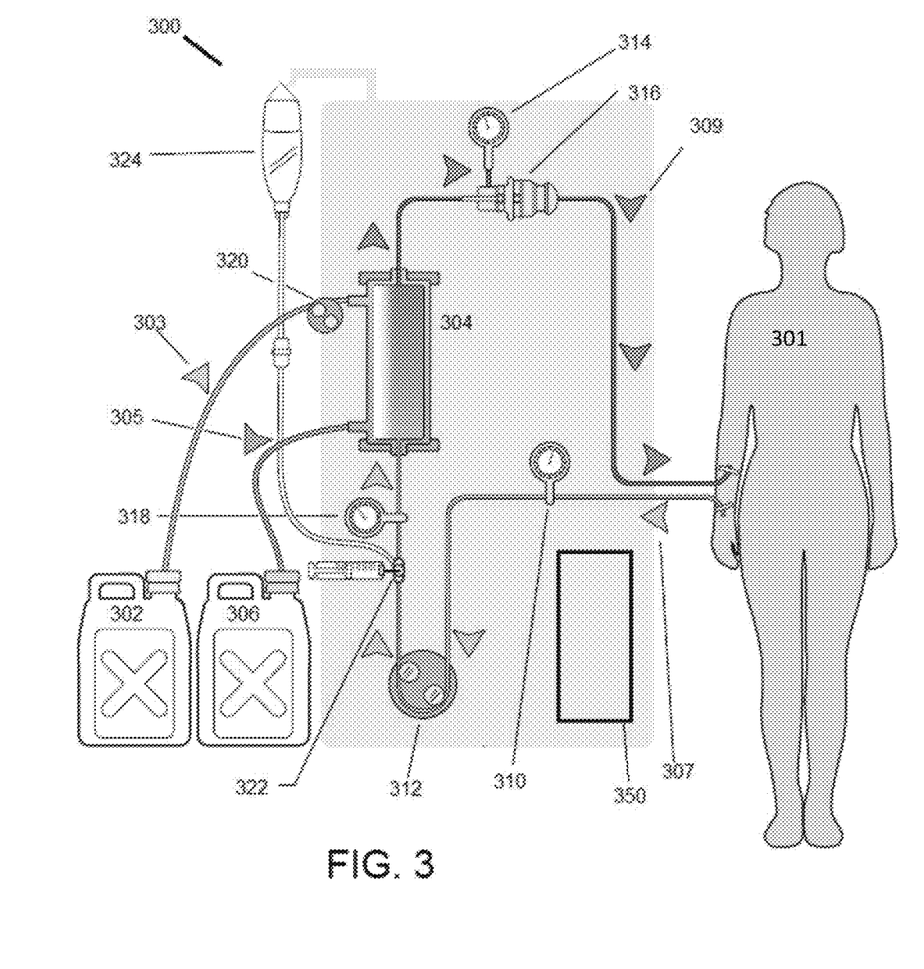
FIG. 3 illustrates another exemplary embodiment of a dialysis system in accordance with the present disclosure.

FIG. 3 illustrates a diagram of an exemplary embodiment of a dialysis system 300 in accordance with the present disclosure. The dialysis system 300 may be configured to provide hemodialysis treatment to a patient 301. Fluid reservoir 302 may deliver fresh dialysate to a dialyzer 304 via tubing 303, and reservoir 306 may receive spent dialysate once it has passed through the dialyzer 304 via tubing 305. A hemodialysis operation may filter particulates and/or contaminates from a patient's blood through a patient external filtration device, for example, a dialyzer 304. As the dialysate is passed through the dialyzer 304, so too unfiltered patient blood is passed into the dialyzer via tubing 307 and filtered blood is returned to the patient via tubing 309. Arterial pressure may be monitored via pressure sensor 310, inflow pressure monitored via sensor 318, and venous pressure monitored via pressure sensor 314. An air trap and detector 316 may ensure that air is not introduced into patient blood as it is filtered and returned to the patient 301. The flow of blood and the flow of dialysate are controlled via respective pumps, including a blood pump 312 and a fluid pump 320. Heparin 322, a blood thinner, may be used in conjunction with saline 324 to ensure blood clots do not form or occlude blood flow through the system.

In some embodiments, the treatment system 300 may include a controller 350, which may be similar to the controller 105 described above with respect to dialysis machines 100, 200. The controller 350 may be configured to monitor fluid pressure readings to identify fluctuations indicative of patient parameters, such as heart rate or respiration rate, or both. For example, a heart rate may be identified individually, a respiration rate may be identified individually, or both the heart rate and the respiration rate may be identified. In some embodiments, a patient heart rate and/or respiration rate may be determinable by the fluid pressure in the tubing or fluid bags, or both. For example, patient parameters may be determinable based on fluid pressure only in the tubing, or may be determinable based on fluid pressure only in the fluid bags, or may be determinable based on fluid pressure in both the tubing and the fluid bags. The controller 350 may also be operatively connected to and/or communicate with additional sensors or sensor systems, although the controller 350 may use any of the data available on the patient's biologic functions or other patient parameters to determine sleep state or monitor safety parameters.

In some embodiments, the operation of the pumps 312 and 320 may generate the greatest noise during a hemodialysis operation. The controller 350 may therefore be tailored to manage the masking sound relative to activation of the pumps 312 and 320. In other embodiments, other operations may generate noise in excess of a threshold noise level, including but not limited to running enclosure cooling fans. The controller 350 may therefore be configured to provide a masking sound for noise cancellation of the components, as described above.

Figure 4:
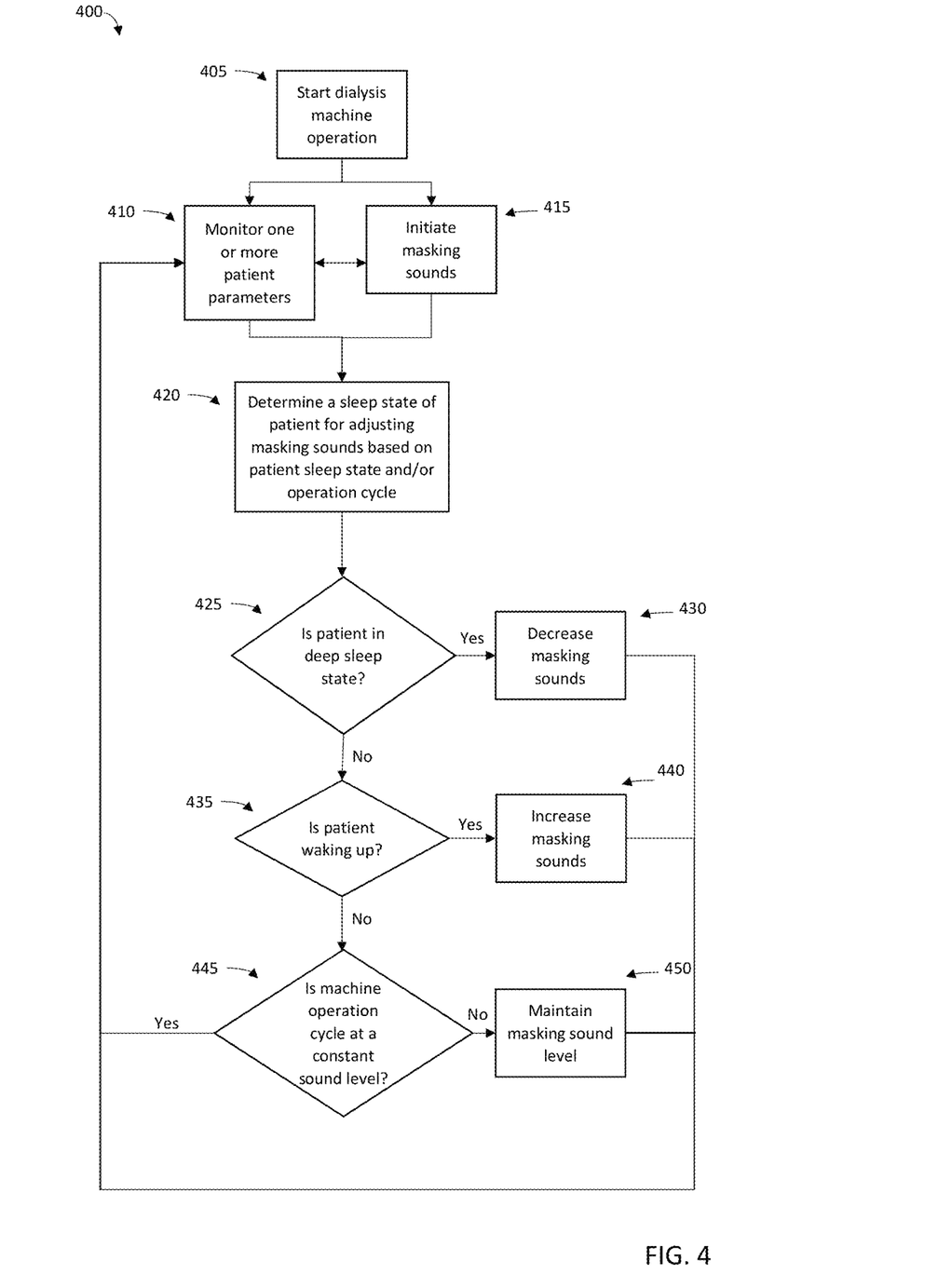
FIG. 4 illustrates a flow diagram of a process for monitoring and adjusting a masking sound during a dialysis operation in accordance with the present disclosure.

Referring now to FIG. 4, a flowchart 400 illustrating an exemplary embodiment of a method of operating a dialysis machine, e.g., like that of any of the dialysis machines 100, 200, 300, described above, in accordance with the present disclosure is shown. At step 405, the machine 100, 200, 300 may begin operation for treatment, e.g., a dialysis treatment operation. The machine 100, 200, 300 may be separate from the controller 105, 350. In some embodiments, the controller 105, 350 may be embedded in the machine 100, 200, 300.

As described above, the dialysis operation may be a peritoneal dialysis or hemodialysis operation. As operation begins, the machine 100, 200, 300 may monitor one or more patient parameters at step 410. As described, the sensors 140 may allow any of a fluid pressure, a heart rate, and/or a respiration rate, or other patient parameters, to be periodically or constantly monitored through the duration of the dialysis operation. In some examples, the sensor data (e.g., pressure data) is analyzed to determine a heart rate and/or respiration rate for the patient. According to one embodiment, fluctuations in pressure readings may be correlated to heart rate and/or respiration rate. In further embodiments, large pressure changes may be correlated with patient movement. For example, a peritoneal dialysis system may include pressure sensors to monitor dialysate pressure in the patient's peritoneal cavity. In cases where multiple sensors are employed, sensor data from the additional sensors may be accessed to, for example, augment pressure sensor data or confirm pressure sensor data, and optionally, may be used instead of or without pressure sensor data.

At step 415, which may occur substantially simultaneously with beginning monitoring the one or more patient parameters 410 at the beginning of the dialysis operation, the machine 100, 200, 300, may initiate a masking sound. As the machine 100, 200, 300 begins operating, a noise may typically be generated as the components, including but not limited to the pumps, fans, air compressor, controller, and the like, are started. Since the home dialysis operation is typically done at night while a patient is sleeping, the patient, and any co-sleepers, may be ready to fall asleep when the dialysis operation begins. The masking sound may thus be initiated at the beginning of the dialysis operation to assist in relaxing the patient and aid in entering a sleep state. It is also understood though that in some embodiments the masking sound may be initiated at any point in the dialysis operation, depending on patient preference.

The machine 100, 200, 300 may determine a sleep state of the patient (and/or a co-sleeper) at step 420. This may indicate to the machine 100, 200, 300, that the patient has fallen asleep, and may begin to adjust the masking sound based on the sleep state and operation cycle in steps 425, 430, 435, 440, 445, and 450. The determination of the sleep state of the patient may be made by analyzing the sensor data to identify transitions between sleep states (e.g., transitions in sleep stages), by determining ranges of patient parameters, such as biologic readings, that correspond to a specific sleep state, or with analysis of transitions and ranges of sensor readings. As discussed above, determination of sleep state may be augmented by additional sensors (e.g., video, thermal imaging, respiration, heart rate, EEG, thermal, motion, audio, etc.). Determination of sleep state may include analysis of any available sensor data. In some embodiments, patients may link their mobile device (e.g., smart phones, tablets, fitness devices, etc.) or home computer systems (e.g., desktop, laptop, home security, etc.) to the machine 100, 200, 300, controller 105, 350, e.g., to allow access to any attached sensor or application. In some examples, determination of sleep state may include image processing and/or image analysis of still photos, video, thermal imaging, etc.

At step 425, the machine 100, 200, 300 determines whether the patient is in a deep sleep state, by monitoring the one or more patient parameters. If the machine 100, 200, 300 determines the patient has entered a deep sleep state, the masking sound may be decreased at step 430, and back to monitoring the one or more patient parameters at step 410. If not, the machine 100, 200, 300 may determine at step 435 if the patient is waking up. If so, the machine 100, 200, 300 may increase masking sounds at step 440, and then resume monitoring the one or more patient parameters at step 410. Increasing masking sounds when the patient is indicated as waking up may encourage the patient to instead fall into a deeper sleep state. If not, at step 445, the machine 100, 200, 300 may determine whether the machine 100, 200, 300 is operating at a constant sound level. If the sound level is changing, at step 450 the masking sound level may be maintained so that the patient may be encouraged to fall into a deeper sleep state. If the machine 100, 200, 300, is operating at a constant sound level, then the method resumes to monitoring the one or more patient parameters at step 410.

The masking sounds may be adjusted throughout the dialysis operation, based on dynamic feedback of the monitoring of the patient parameters. The monitoring may end when the dialysis operation completes. This may improve a patient's sleeping experience, as it may be customized to the patient's individual sleeping patterns and preferences.

Some embodiments of the disclosed system may be implemented, for example, using a storage medium, a computer-readable medium or an article of manufacture which may store an instruction or a set of instructions that, if executed by a machine (i.e., processor or microcontroller), may cause the machine to perform a method and/or operations in accordance with embodiments of the disclosure. In addition, a server or database server may include machine readable media configured to store machine executable program instructions. Such a machine may include, for example, any suitable processing platform, computing platform, computing device, processing device, computing system, processing system, computer, processor, or the like, and may be implemented using any suitable combination of hardware, software, firmware, or a combination thereof and utilized in systems, subsystems, components, or sub-components thereof. The computer-readable medium or article may include, for example, any suitable type of memory unit, memory device, memory article, memory medium, storage device, storage article, storage medium and/or storage unit, for example, memory (including non-transitory memory), removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A dialysis machine, comprising:
   tubing or a fluid container, or both, being connectable to a patient for flowing fluid to or from the patient;
   one or more sensors configured to detect one or more patient parameters; and
   a controller configured to:
     determine a sleep state of the patient based on the one or more patient parameters detected by the one or more sensors; and
     adjust a masking sound in response to the sleep state of the patient;
   wherein the masking sound is activatable in response to noise generated during operation of the dialysis machine.

2. The dialysis machine according to claim 1, wherein the one or more patient parameters include a fluid pressure, a heart rate, or a respiration rate, or combinations thereof.

3. The dialysis machine according to claim 1, wherein the one or more patient parameters are detected directly by the one or more sensors.

4. The dialysis machine according to claim 1, wherein the one or more patient parameters are determined indirectly by the one or more sensors.

5. The dialysis machine according to claim 1, wherein the one or more sensors are configured for periodic monitoring or continuous monitoring, or both.

6. The dialysis machine according to claim 1, wherein a sleep state is a light sleep state, a state where eye movement is stopped, a deep sleep state, or a REM sleep state, or combinations thereof.

7. The dialysis machine according to claim 6, wherein the masking sound is adjustable by increasing the masking sound in response to the controller determining the patient is not in the deep sleep state.

8. The dialysis machine according to claim 6, wherein the masking sound is adjustable by decreasing the masking sound in response to the controller determining the patient is in the deep sleep state.

9. The dialysis machine according to claim 1, wherein the controller is configured to determine a sleep state of one or more persons in a vicinity of the dialysis machine, and wherein the one or more persons is unconnected to the tubing or fluid container, or both.

10. The dialysis machine according to claim 1, wherein the one or more sensors includes a pressure sensor configured to detect a pressure of the fluid.

11. The dialysis machine according to claim 10, wherein the controller is configured to determine a heart rate or a respiration rate, or both, based on the monitored fluid pressure by the pressure sensor.

12. The dialysis machine according to claim 11, wherein the sleep state is determinable by the controller based on the heart rate or the respiration rate, or both.

13. The dialysis machine according to claim 1, wherein the masking sound is a noise cancelling frequency, music, podcast, audio book, or pre-recorded sounds, or combinations thereof.

14. The dialysis machine according to claim 1, wherein the masking sound is receivable to the dialysis machine from a remote device.

15. The dialysis machine according to claim 1, wherein the noise generated during operation of the dialysis machine is generated by a pump, a fan, an air compressor, or the controller, or combinations thereof.

16. A method for operating a dialysis machine, a patient being connected to tubing or a fluid container, or both, for flowing fluid to or from the patient, comprising:
monitoring one or more patient parameters by one or more sensors;
initiating a masking sound in response to noise generated during operation of the dialysis machine;
determining a sleep state of the patient by a controller, based on the one or more patient parameters detected by the one or more sensors; and
adjusting the masking sound by the controller in response to the sleep state of the patient.

17. The method according to claim 16, wherein the one or more patient parameters include a fluid pressure, a heart rate, or a respiration rate, or combinations thereof.

18. The method according to claim 16, wherein the one or more patient parameters are detected directly by the one or more sensors.

19. The method according to claim 16, wherein the one or more patient parameters are determined indirectly by the one or more sensors.

20. The method according to claim 16, wherein the one or more sensors are configured for periodic monitoring or continuous monitoring, or both.

21. The method according to claim 16, wherein a sleep state is a light sleep state, a state where eye movement is stopped, a deep sleep state, or a REM sleep state, or combinations thereof.

22. The method according to claim 21, wherein the masking sound is adjustable by increasing the masking sound in response to the controller determining the patient is not in the deep sleep state.

23. The method according to claim 21, wherein the masking sound is adjustable by decreasing the masking sound in response to the controller determining the patient is in the deep sleep state.

24. The method according to claim 16, wherein the controller is configured to determine a sleep state of one or more persons in a vicinity of the dialysis machine, and wherein the one or more persons is unconnected to the tubing or fluid container, or both.

25. The method according to claim 16, wherein the one or more sensors includes a pressure sensor configured to detect a pressure of the fluid.

26. The method according to claim 25, wherein the controller is configured to determine a heart rate or a respiration rate, or both, based on the monitored fluid pressure by the pressure sensor.

27. The method according to claim 26, wherein the sleep state is determinable by the controller based on the heart rate or the respiration rate, or both.

28. The method according to claim 16, wherein the masking sound is a noise cancelling frequency, music, podcast, audio book, or pre-recorded sounds, or combinations thereof.

29. The method according to claim 16, wherein the masking sound is receivable to the dialysis machine from a remote device.

30. The method according to claim 16, wherein the noise generated during operation of the dialysis machine is generated by a pump, a fan, an air compressor, or the controller, or combinations thereof.

* * * * *